US006749571B2

United States Patent
Varghese et al.

(10) Patent No.: US 6,749,571 B2
(45) Date of Patent: Jun. 15, 2004

(54) METHOD AND APPARATUS FOR CARDIAC ELASTOGRAPHY

(75) Inventors: Tomy Varghese, Madison, WI (US); Christian S. Breburda, Madison, WI (US); James A. Zagzebski, Madison, WI (US); Peter Samuel Rahko, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/247,693

(22) Filed: Sep. 19, 2002

(65) Prior Publication Data
US 2004/0059224 A1 Mar. 25, 2004

(51) Int. Cl.$^7$ .................................................. A61B 8/06
(52) U.S. Cl. ........................................................ 600/450
(58) Field of Search ................................ 600/437, 438, 600/440, 441–449, 454–456; 73/619–626

(56) References Cited

U.S. PATENT DOCUMENTS 5,513,640 A    5/1996  Yamazaki et al.
6,277,074 B1 * 8/2001  Chaturvedi et al. ......... 600/437
2003/0013963 A1 1/2003  Bjaerum et al.

FOREIGN PATENT DOCUMENTS

EP    1 079 240 A2   2/2001

OTHER PUBLICATIONS

Kani, Hiroshi, et al., Noninvasive Evaluation of Local Myocardial Thickening and Its Color–Coded Imaging, IEEE Transactions on Ultrasonics, Ferroelectrics, and Frequency Control, vol. 44, No. 4, Jul. 1997.

* cited by examiner

Primary Examiner—Ali Imam
(74) Attorney, Agent, or Firm—Quarles & Brady LLP

(57) ABSTRACT

Elastographic imaging of heart tissue may be used to provide strain images by mapping strain magnitude to brightness and strain sign to hue and thus provide improved clinical indication of compression and distension of heart muscle. An areal cursor may be used to obtain quantitative measurements of strain at predetermined periods in the heart cycle. Multiple area measurements of strain may be combined to provide a quantitative index of cardiac health.

21 Claims, 2 Drawing Sheets

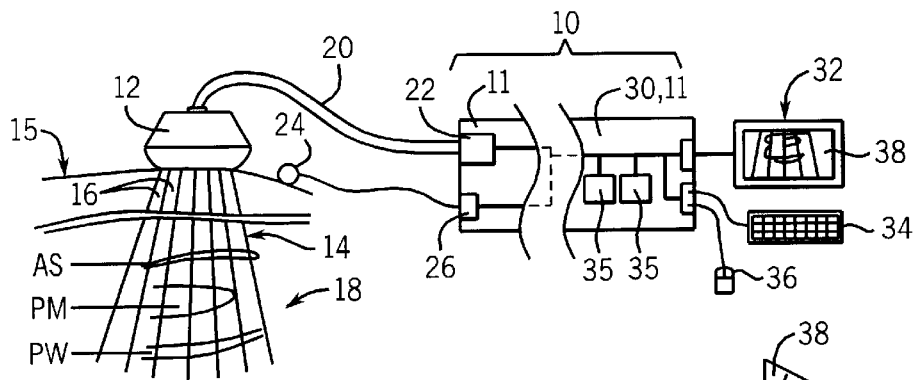
FIG. 1
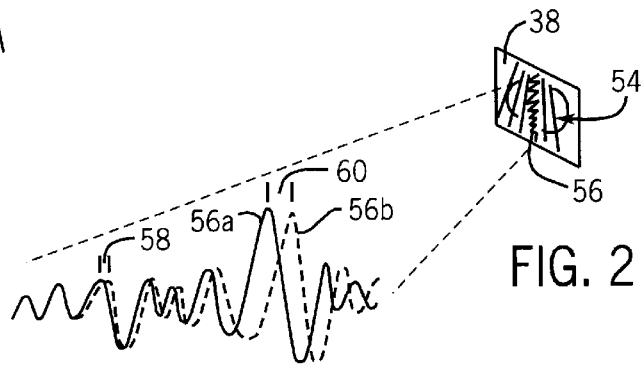
FIG. 2
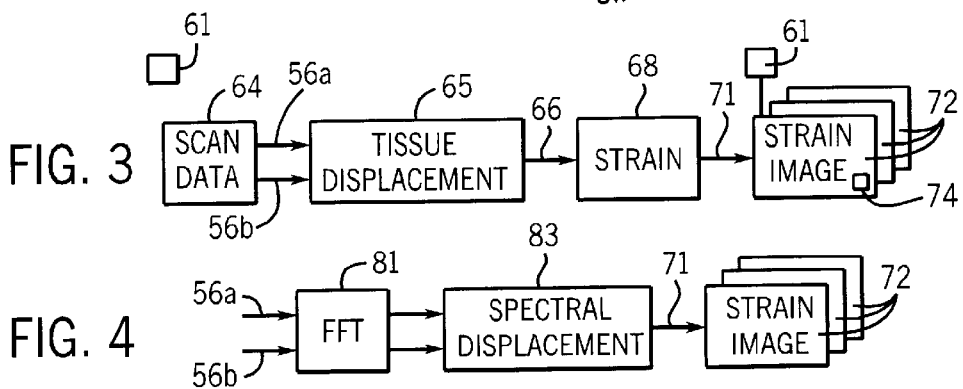
FIG. 3
FIG. 4
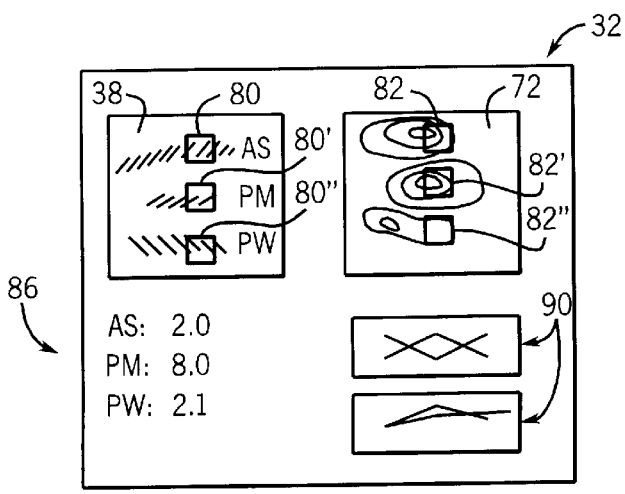
FIG. 5

| STRAIN | BRIGHTNESS | HUE |
|---|---|---|
| +3 | 3 | YELLOW |
| +2 | 2 | ORANGE |
| +1 | 1 | RED |
| 0 | 0 | - |
| −1 | 1 | VIOLET |
| −2 | 2 | BLUE |
| −3 | 3 | INDIGO |
FIG. 6
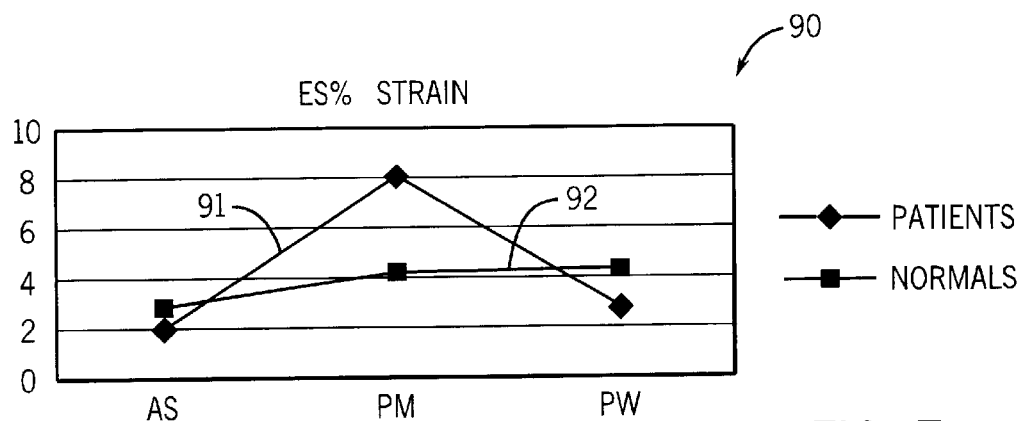
FIG. 7
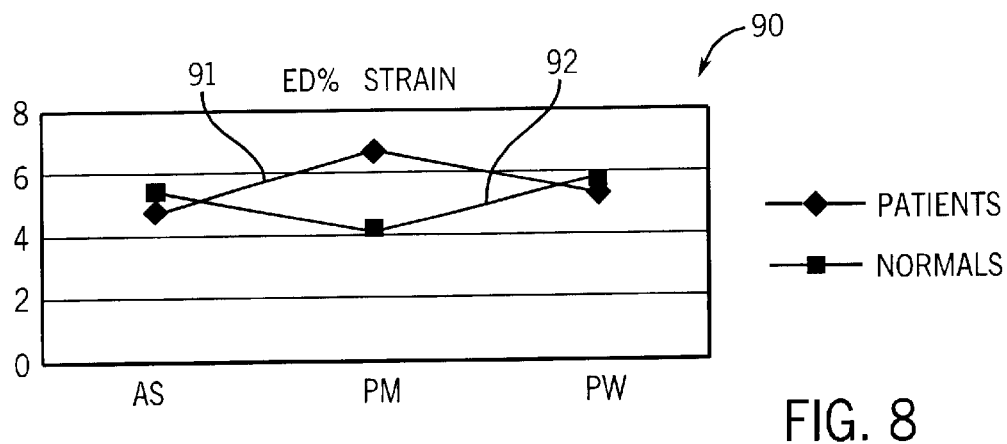
FIG. 8

METHOD AND APPARATUS FOR CARDIAC ELASTOGRAPHY

STATEMENT REGARDING FEDERALLY SPONSORED RESEARCH OR DEVELOPMENT

This invention was made with United States government support awarded by the following agencies: NIH CA 39224. The United States has certain rights in this invention.

CROSS-REFERENCE TO RELATED APPLICATIONS

BACKGROUND OF THE INVENTION

The present invention relates to a device for medical imaging and diagnosis, and in particular, to the use of elastography for the evaluation of cardiac health.

Elastography is a new imaging modality that reveals the stiffness properties of tissues, for example, axial strain, lateral strain, Poisson's ratio, Young's modulus, or other common strain and strain related measurements. The strain measurements may be collected over an area and compiled as a two-dimensional array of data, which may then be mapped to a gray scale to form a strain "image".

In "quasi static" elastography, two conventional images of the tissue are obtained using ultrasound, computed tomography (CT), or magnetic resonance imaging (MRI). The first image provides a base line of the tissue at a given state of compression or distention and the second image is obtained with the tissue under a different compression or distention. The tissue may be compressed by an external agency such as a probe or the like or may be compressed by its own muscular action, for example, in the case of the heart, or by movement of adjacent organs. Displacement of the tissue between the two images is used to deduce the stiffness of the tissue. Quasi-static elastography is thus analogous to a physician's palpation of tissue in which the physician determines stiffness by pressing the tissue and detecting the amount that the tissue yields under this pressure.

In "dynamic" elastography, a low frequency vibration is applied to the tissue and the tissue vibrations accompanying the resulting elastic wave are measured, for example, using ultrasonic Doppler detection.

Elastography has recently been investigated as a method of detecting cardiac dysfunction. Normal, periodic myocardial thickening, associated with proper heart function, may be revealed in the strains shown in an elastographic image. Tissue ischemia or infarction may thus be detected as a reduction of myocardial thickening.

Despite the promise of elastography for cardiac evaluation, effective methods for displaying myocardial strain and of relating elastographic measurements to cardiac disease have not yet been developed.

BRIEF SUMMARY OF THE INVENTION

The present invention provides an improved method and apparatus for producing elastographic images of the heart to detect cardiac disease.

The invention includes in its several embodiments: a visually improved mapping of the two dimensions of strain (direction and sign) to a color scale, an area cursor quantifying strain measurements within predefined regions, and a quantitative metric of cardiac function comparing different predefined heart regions to reduce operator variability in the assessment of cardiac disease.

Specifically, the present invention provides an elastography apparatus including a medical imaging system, operating on in vivo tissue, to provide at least a two-dimensional array of strain values related to points in the tissue. Each strain value has a magnitude and sign indicating an amount of strain at a point and whether the strain is compression or distension, respectively. The apparatus further includes an image generator mapping the array of strain values to colors at pixels in an image such that brightness of the colors varies monotonically with absolute value (magnitude) strain value and hue of the colors is related to strain value sign.

Thus, it is one object of the invention to provide a visually intuitive color mapping for strain by independently mapping two dimensions of strain to brightness and hue.

Zero absolute value strain may map to black.

It is another object of the invention to visually de-emphasize regions of low strain.

The compressive tissue strain may map to warm hues and distensive tissue strain may map to cool hues.

It is thus another object of the invention to provide a clear visual distinction between compressive and distensive strains.

In one embodiment, the signal processing circuitry may provide a second image of the heart tissue indicating relatively time invariant tissue quantities.

Another object of the invention can be to provide a separate image to serve as a point of reference for the strain image.

The two images may be side-by-side on a single display device and a first and second movable cursor may be superimposed on corresponding regions of the images.

The two images may also be superimposed on a single display device with a cursor used to navigate about the strain image, with the wall location identified by the gray-scale ultrasound image.

Thus, it is another object of the invention to simplify navigating about the strain image. One of the cursors can be located on a region identified in the conventional image to locate the corresponding region in the strain image.

The cursor may define a region of interest and the signal processing circuitry may provide a quantitative display of strain of tissue within the region of interest.

Thus, it is another object of the invention to provide a quantitative and less observer dependent measurement of tissue strain.

The apparatus may include a means for identifying a phase of the beating heart and the quantitative display may be related to the phase of the beating heart. For example, the quantitative display may provide an indication of strain of the tissue within the region of interest at the end of the systolic phase or the end of the diastolic phase of the beating heart.

It can thus be another object of the invention to provide a robust repeatable measurement of strain that may be useful for generating a standardized index for cardiac function.

The apparatus may provide strain measurements at several predefined regions in the heart tissue. The quantitative display may then be a comparison of strains in these regions.

Thus, it is another object of the invention to provide a standardized index for cardiac function that makes use of a multi-point quantitative assessment, difficult for an unassisted observer.

These particular objects and advantages may apply to only some embodiments falling within the claims and thus do not define the scope of the invention.

BRIEF DESCRIPTION OF THE DRAWINGS

FIG. 1 is a simplified block diagram of an ultrasound scanner suitable for use with the present invention in scanning heart tissue;

FIG. 2 is a graphical representation of an ultrasonic signal received by the ultrasound scanner of FIG. 1 showing the analysis of one waveform of the signal taken at two successive times with different strain of the heart tissue showing a shifting of the signals corresponding to such strain;

FIG. 3 is a block diagram of the processing of the scan data of FIG. 2 by the ultrasound scanner of FIG. 1 to deduce stiffness using a time-domain analysis technique;

FIG. 4 is a figure similar to that of FIG. 3 using a frequency domain analysis technique;

FIG. 5 is a representation of the screen of the display of the apparatus of FIG. 1 showing a juxtaposed conventional, and strain tissue images and showing tracking cursors for navigation and quantitative display of the strain measurement in numerical and graphical form;

FIG. 6 is a table indicating a mapping of strain data to color of the strain image of FIG. 5; and FIGS. 7 and 8 are detailed presentations of the graphical forms of quantitative display of FIG. 5.

DETAILED DESCRIPTION OF THE PREFERRED EMBODIMENT

Referring now to FIG. 1, an ultrasonic imaging system 10 suitable for use with the present invention may include a standard ultrasound machine 11 alone or in combination with a stand-alone computer 30. Generally, the ultrasonic imaging system 10 provides a graphic display 32, a keyboard 34 for data entry and a cursor control device 36, such as a mouse, as is well understood in the art for providing user input.

The ultrasound machine 11 forming part of the ultrasonic imaging system 10 may be a GE Vingmed Vivid FiVe ultrasound system (commercially available from GE Vingmed of Forton, Norway) communicating with a 2.5 Megahertz phased array transducer 12 transmitting and receiving a beam 14 of ultrasonic energy along a number of rays 16. For cardiac imaging, the transducer 12 is placed against a patient 15 and directed in to provide an apical or parasternal view of the heart 18. In the latter, parasternal or long axis view, a measurement of the anterior septal (AS) wall, the posterior medial papillary muscle (PM), and the posterior wall (PW) may be made.

As is understood in the art, during each data acquisition, the transducer 12 transmits an ultrasound beam 14 into the heart 18 and receives echo data at each of numerous transducer elements. This data is transmitted via cable 20 to the ultrasonic imaging system 10 where it is received and processed by interface circuitry 22. Alternatively, echo data are formed into signals representing echoes from along each of the rays 16 and then transmitted to imaging system 10. In the preferred embodiment, the data may be sampled at twenty megahertz or higher, and repeated acquisitions are taken at a frame rate of at least 50 frames per second.

The patient 15 may also have ECG electrodes 24 attached to the patient's skin for the acquisition of electrocardiogram data received by acquisition circuit 26. Such ECG data will be keyed to the acquired ultrasound data so that it is referenced to a phase of the heartbeat.

The processed ultrasound data will be assembled into conventional B-mode images 38 providing a real-time representation of a plane through the heart 18 according to well-known techniques. Further processing, according to the present invention (as will be described below), may be performed by a processor 33 executing a stored program contained in memory 35 residing either in the standard ultrasound machine 11 or the stand-alone computer 30.

Referring now also to FIG. 2, each image 38 is composed of a series of time-domain signals 56 corresponding approximately with the rays 16, and having a varying amplitude mapped to brightness of pixels 54 forming the columns of the image 38. As such, the time axis of each signal 56 generally reflects distance from the ultrasound transducer 12 to the tissue of the heart 18.

The strain within the tissue of the heart 18 may be determined by comparing corresponding time-domain signals 56a and 56b from two sequential ultrasound echo images 38 measuring the heart tissue at different degrees of compression during its normal beating phase. As shown, the second time-domain image signal 56b exhibits an expansion in time reflecting an expansion or distention of the heart tissues away from the ultrasound transducer 12. More generally, the later time-domain image signal 56b might represent either relative distention or relative compression with respect to earlier time-domain image signal 56a.

A general translation of the tissue of the heart 18 (rather than local compression or distension) would cause an equal offset between all points in time-domain image signal 56a and 56b. However, the elasticity of the tissue causes local tissue compression or distension, which in turn produces a gradient in the phase offset of the time-domain image signals 56a and 56b as a function of time and distance from the ultrasound transducer 12.

For the example shown, the phase offset 58 between the time-domain image signals 56a and 56b at early times and hence near the ultrasound transducer 12 will be smaller than the phase offset 60 at later times and for tissue further away from the ultrasound transducer 12. The rate of change of these displacements at points over the region of the heart 18 provides a series of strain values having magnitude and sign that may be used to produce an elastographic image of the tissue of the heart 18.

Referring to FIG. 3, more specifically, ultrasonic scan data 64 is collected being at least two images 38 containing successive time-domain image signals 56a and 56b, the latter linked to ECG data 61. At process block 65, these signals are processed to determine tissue displacement along an axis from the ultrasound transducer 12 through the heart 18. In principle, short segments of the time-domain image signals 56a and 56b are analyzed by moving one segment with respect to the other until a best match is obtained and the amount of movement needed for the best match determines tissue displacement. The matching process may be implemented by means of mathematical correlation of the segments.

The displacement of signal 66 output by process block 65 is further processed by the process block 68, which determines strain as a gradient of the displacement signal. The strain values 71 may be mapped to an elastic graphic image 72 also linked to the ECG signal 61 and thus having a defined phase with respect to the heartbeat.

As each successive frame is obtained by the system of FIG. 1, a new elastic graphic image may be obtained by comparing that frame to the predecessor frame to determine displacement as has been described, and thus the strain is relative to the last image 38. Alternatively, a base image approximating the heart at rest may be used to produce strain relative to that image or a peak or root-mean-square value or other similar measure can be adopted.

Referring momentarily to FIG. 4, alternative algorithms may be used to create the elastographic images 72. In one such algorithm, the time-domain image signals 56a and 56b may be received by process block 81 to extract a spectra of the time-domain image signals 56a and 56b using, for example, the well-known fast Fourier transform algorithm. The spectra of the time-domain image signals 56a and 56b will be shifted according to the Fourier transformation property that causes dilation in a time-domain signal to produce a down-frequency shift in its frequency-domain spectrum. The amount of shift may be determined at process block 83 using correlation techniques similar to those used in process block 65 but executed on the frequency-domain signals.

The shift between the spectra taken of different segments of the time-domain signals 56a and 56b centered at increasing time delays, provides a gradient signal to produce elastographic images 72. While the results are similar to the technique of FIG. 3, this approach may have some advantages in terms of robustness against noise and the like.

Each of these process blocks may be implemented through a combination of hardware and software in the ultrasonic imaging system 10 and/or the stand-alone computer 30 as is well understood to those of ordinary skill in the art.

Referring now to FIGS. 3 and 6, the strain values 71 for each pixel 74 of the images 72 will have a magnitude and sign. The magnitude indicates the amount of the distension or compression of the tissue and the sign indicates whether it is a compression or distention with positive signs normally denoting compression and negative signs by convention noting distension of the tissue. FIG. 6 provides a mapping table 89 used in at least one embodiment of the present invention accepting as arguments compressive strains positive one through three and distensive strains negative one through three. The mapping table 89 maps the absolute value of the strains (magnitude) to brightness of the corresponding pixels 74 in the elastographic image 72 and maps the sign of the strains to particular hues for the corresponding pixels 74. In a preferred embodiment strains with positive signs (indicating compression) map to warm hues such as yellow, orange, and red, and strains with negative signs (indicating distension) map to cool hues such as violet, blue, and indigo.

The brightness is the perceived brightness of the pixel 74 and this may be affected in part by the hues, as the eye is more sensitive to some hues than it is to others. For this reason, the ordering of the hues may be selected to augment the intended brightness. Generally, it is desired that the brightness be monotonic meaning that it only increases or only decreases for each of the positive and negative ranges.

This system can be contrasted to a color mapping scheme in which a full range of hues are mapped to the full range of strain, for example, by applying the full spectrum red, orange, yellow, green, blue, indigo, and violet, to the full range of strains from negative three to positive three. The advantage of the present system is that the peak strains both positive and negative are emphasized. Regions of positive and negative strain tend to separated by black or dark moats of color.

Referring now to FIGS. 1 and 5, the processor 33 executing the stored program in memory 35 may juxtapose the conventional B-mode image 38 (typically in a gray scale) next to a elastographic image 72 and also provide for a series of cursors 80 and 82 that may be positioned over the images 38 and 72, respectively, through the use of the cursor control device 36 and keyboard 34. The images 38 and 72 may be updated in real time and sized and oriented to show the same region of heart tissue. Image 38 shows relatively time invariant qualities of the heart tissue, such as tissue interfaces, and further provides a higher resolution image of the heart in which anatomical features may be more readily distinguished. Cursor 80 and 82, in any case, are positioned to track each other so as to constantly contain a region of interest 84 centered on the same structure in both the images 38 and 72. In this manner, the image 38 may be used to identify particular anatomy of the heart 18 and the strain may be investigated by reviewing the region within the cursor 82.

A quantitative readout 86 may be provided on the graphics display 32 providing statistics related to the strain of the tissue contained in the region of interest of the cursor 82. In the simplest embodiment, a current strain relative to the last image 38 may be displayed or alternatively a peak strain, absolute strain, or average strain magnitude may be displayed.

Alternatively and in the preferred embodiment, a strain value at a particular phase of the beating of the heart 18 may be displayed at quantitative readout 86 through the use of the keyed electrocardiograph data 61 linked to the images 72. Preferably, the strain measured at the end of the systolic or end of the diastolic heartbeat phases may be used. Selection of these times provides large strain values providing an improved signal to noise ratio and a consistent and repeatable point at which strain may be measured quantitatively.

Multiple cursors 80 and 82 may be used as part of an index to provide a standard measurement of cardiac function. In this embodiment, one cursor 80 is placed in the anterior septal wall of the heart. A second cursor is 80' is placed on the posterior medial papillary muscle and a third cursor 80' is placed on the posterior wall of the heart 18 as guided by image 38. Corresponding cursors 82, 82', and 82" appear in the image 72.

Measurements of strain in each of these cursor locations is then obtained at the end of the systole and end of the diastole and this data is presented in graphs 90 also shown on graphics display 32.

Referring now to FIG. 7, the plot 91 of strain values at the end of systole for a patient having coronary artery disease may be readily distinguished from the plot 92 derived from a group of normal patients having no cardiac dysfunction.

Likewise, referring to FIG. 8, the plot 91 of strain values at the end of diastole for a patient having coronary artery disease may be readily distinguished from the plot 92 derived from a group of normal patients having no cardiac dysfunction The data of these graphs may be distilled to a single quantitative number that may be empirically related to cardiac dysfunction and displayed as well.

It is specifically intended that the present invention not be limited to the embodiments and illustrations contained herein, but include modified forms of those embodiments including portions of the embodiments and combinations of elements of different embodiments as come within the scope of the following claims. For example, the present invention though preferably used with ultrasonic elastography, has application for Doppler and other kinds of elastography and may be used with both transmission and reflection ultrasound.

We claim:

1. An elastography apparatus comprising:
   a medical imaging system operating on in vivo tissue to provide at least a two-dimensional array of strain values related to points in the tissue, each strain value having magnitude and a sign indicating an amount of strain at a point and whether the strain is compression or distension, respectively; and an image generator mapping the array of strain values to colors at pixels in an image such that brightness of the colors varies monotonically with strain value absolute value, and hue of the colors is related to strain value sign.

2. The elastography apparatus of claim 1 wherein the image generator maps zero absolute value strain to black.

3. The elastography apparatus of claim 1 wherein the medical imaging system is an ultrasound scanner producing a series of a real-time tissue images and comparing the tissue images to determine the array of strain values.

4. The elastography apparatus of claim 1 wherein the image generators maps compressive strain values to warm hues, and distensive strain values to cool hues.

5. The elastography apparatus of claim 1 wherein the image generator further provides a second image of the tissue indicating substantially time invariant tissue qualities.

6. The elastography apparatus of claim 1 wherein the second image is a gray-scale image.

7. The elastography apparatus of claim 1 wherein the color image indicating strain and the second image are of identical regions of the tissue juxtaposed on a single display device.

8. The elastography apparatus of claim 7 wherein the image generator further provides a first and second movable cursor superimposed on corresponding regions of both the color image indicating strain and the second image, the cursors defining a region of interest.

9. The elastography apparatus of claim 8 wherein the image generator further provides a quantitative display of strain of the tissue within the region of the cursor in the color image.

10. An echocardiography apparatus comprising:
an ultrasonic transducer for receiving an ultrasonic signal modified by passage through heart tissue;
signal processing circuitry communicating with the ultrasonic transducer and a display, and operating to determine values of strain in the heart tissue and to provide on the display:
(a) an image of the heart tissue indicating tissue locations;
(b) a movable cursor superimposed on the image of the heart tissue to define a region of interest; and
(c) a quantitative display of strain of the tissue within the region of interest.

11. The echocardiography apparatus of claim 10 further including a means for identifying a phase of the beating heart tissue and wherein the quantitative display is related to a phase of the beating heart.

12. The echocardiography apparatus of claim 10 wherein the signal processing circuitry further provides a second movable cursor superimposed on the image of the heart tissue to define a second region of interest; and
a second quantitative display relating the strain of the tissue within the region of interest to the strain in the second region of interest.

13. The echocardiography apparatus of claim 12 wherein the second quantitative display is a graph.

14. The echocardiography apparatus of claim 12 wherein the second quantitative display is a comparison to a normal population.

15. The echocardiography apparatus of claim 12 further including a means for identifying a phase of the beating heart tissue and wherein the second quantitative display is related to the phase of the beating heart.

16. The echocardiography apparatus of claim 15 wherein the second quantitative display provides an indication of relative strain at a time selected from the group consisting of: the end systolic phase of the beating heart and the end diastolic phase of the beating heart tissue.

17. An echocardiography apparatus comprising:
an ultrasonic transducer for receiving an ultrasonic signal modified by passage through heart tissue;
signal processing circuitry communicating with the ultrasonic transducer and a display and operating to determine values of strain in the heart tissue, and to provide on the display, a quantitative display relating the strain of the tissue within at least two predetermined regions of interest in the heart tissue, a relationship of the strain between the regions so as to provide an indication of coronary heart disease.

18. The echocardiography apparatus of claim 17 wherein the predetermined regions of interest are selected from the group consisting of: the anteroseptal wall, the posterior medial papillary muscle and the posterior wall.

19. The echocardiography apparatus of claim 17 wherein the display is a graph.

20. The echocardiography apparatus of claim 17 further including a means for identifying a phase of a beating of the heart tissue and wherein the display is related to the phase of the beating heart.

21. The echocardiography apparatus of claim 17 wherein the display relates the strain of the tissue within the predetermined regions of interest in the heart tissue at a time selected from the group consisting of: the end systolic phase of the beating heart and the end diastolic phase of the beating heart.

* * * * *